United States Patent
Arneberg et al.

(10) Patent No.: US 10,512,401 B2
(45) Date of Patent: Dec. 24, 2019

(54) METHODS AND SYSTEMS FOR FACILITATING MEDICAL CARE

(71) Applicant: Healo, Inc., Hockssin, DE (US)

(72) Inventors: Benjamin Arneberg, Cambridge, MA (US); Ana Patricia Furukawa, Cambridge, MA (US); Nathan Ie, Boston, MA (US); Gino Inverso, Richboro, PA (US); Peter Jackson, Cambridge, MA (US)

(73) Assignee: Parable Health, Inc., Hockssin, DE (US)

( * ) Notice: Subject to any disclaimer, the term of this patent is extended or adjusted under 35 U.S.C. 154(b) by 1636 days.

(21) Appl. No.: 14/269,139

(22) Filed: May 3, 2014

(65) Prior Publication Data

US 2014/0330130 A1 Nov. 6, 2014

Related U.S. Application Data

(60) Provisional application No. 61/819,077, filed on May 3, 2013.

(51) Int. Cl.
*A61B 5/00* (2006.01)

(52) U.S. Cl.
CPC .......... *A61B 5/0013* (2013.01); *A61B 5/0077* (2013.01); *A61B 5/445* (2013.01); *A61B 5/6898* (2013.01); *A61B 5/7465* (2013.01); *A61B 5/7475* (2013.01); *A61B 5/441* (2013.01); *A61B 5/7267* (2013.01); *A61B 5/7425* (2013.01)

(58) Field of Classification Search
CPC .... A61B 5/0013; A61B 5/0077; A61B 5/7475
See application file for complete search history.

(56) References Cited

U.S. PATENT DOCUMENTS

| | | | | |
|---|---|---|---|---|
| 2006/0005168 A1* | 1/2006 | Singh | ............... | G06F 17/30265 717/123 |
| 2008/0194928 A1* | 8/2008 | Bandic | ............... | G16H 15/00 600/306 |
| 2013/0322711 A1* | 12/2013 | Schultz | ............... | G06F 19/3418 382/128 |

* cited by examiner

*Primary Examiner* — Alyssa M Alter
(74) *Attorney, Agent, or Firm* — Danielson Legal LLC

(57) ABSTRACT

Mobile and/or computer based functionality to: (i) provide a secure method of communication between patients and physicians; (ii) provide reminders and/or alerts to patients in the form of mobile phone alerts, mobile phone alarms, email, text messages, etc.; (iii) offer calibrated photo taking using, e.g., shadow-overlay; (iv) utilize historical image data to identify complications or diagnose conditions; and (v) aggregate and present a composite of multiple photos (e.g., a time-lapse profile or gallery).

8 Claims, 7 Drawing Sheets

CREATE APPOINTMENT

LINK PATIENT TO APPOINTMENT

PATIENT TAKES PHOTOS WITH PhotoAssist™ WHEN REMINDED

VIEW APPOINTMENT

PHOTO TIMELINE

PHOTO GALLERY

ZOOMABLE PHOTOS

METHODS AND SYSTEMS FOR FACILITATING MEDICAL CARE

CROSS-REFERENCE TO RELATED APPLICATIONS

The present application claims the benefit of U.S. provisional application No. 61/819,077, filed on May 3, 2013, the entire disclosure of which is incorporated by reference as if set forth in its entirety herein.

FIELD OF THE INVENTION

The present invention is directed toward the field of medical treatment and, in particular, to the use of mobile technologies to improve follow-up medical care.

BACKGROUND OF THE INVENTION

The completion of a medical procedure is not the end of the medical care associated with that procedure. Wound and suture care is of critical importance, as infection, dehiscence and other complications can occur and result in, among other things, discomfort, scarring, and, in severe cases, death. These complications can require repeat follow-up visits or hospitalizations not only to treat the complications, but also to simply detect them. Such visits can be time consuming for both patient and caregiver, as well as costly for patients, insurers, and other parties involved in the provision of and payment for medical care, as described in more detail below.

Follow-up visits also affect doctors and hospitals. Unlike typical visits, doctors and hospitals shoulder the full cost of follow-up visits. This is because follow-up visits fall inside a grace period (otherwise known as the "global period") following the procedure and cannot be reimbursed. Instead of earning money like they would from a typical appointment, doctors and hospitals are losing money on follow-up visits. Each year the U.S. medical system treats tens of millions of surgical and traumatic wounds, establishing follow-up visits not only as a financial burden but also a resource burden given the current shortage of physicians in the U.S. health care system.

Accordingly, for the foregoing reasons it would be desirable to have a technology that would provide a financial and social solution to the burden of follow-up visits.

SUMMARY OF THE INVENTION

This summary is provided to introduce a selection of concepts in a simplified form that are further described below in the Detailed Description section. This summary is not intended to identify key features or essential features of the claimed subject matter, nor is it intended to be used as an aid in determining the scope of the claimed subject matter.

Embodiments of the present invention enable remote monitoring of healing processes and remote follow-up visits by transmitting images of a condition as well as optional patient feedback. The images may be presented in various embodiments as a time-lapse sequence or a gallery. Suitable conditions for monitoring include skin lesions or other conditions. The patient feedback may be transmitted by, e.g., the use of a questionnaire to elicit information from the patient.

In various embodiments, the invention includes mobile and/or computer based applications that: (i) provide a secure method of communication between patients and physicians; (ii) provide reminders and/or alerts to patients in the form of mobile phone alerts, mobile phone alarms, email, text messages, etc.; (iii) offer calibrated photo taking using, e.g., shadow-overlay; (iv) utilize historical image data to identify complications or diagnose conditions; and (v) aggregate and present a composite of multiple photos (e.g., a time-lapse profile or gallery).

In one aspect, the present invention concerns an apparatus for remote medical follow-up. According to this aspect and related aspects, the apparatus includes an interface configured to receive communications specifying a schedule for imaging, and further configured to transmit communications comprising an image, a camera for capturing at least one image, and a user interface for prompting the operator of the apparatus to operate the camera according to the specified schedule.

In various embodiments of this and related aspects, the user interface prompts the operator to respond to at least one inquiry specified by a third party, and the user interface may prompt the operator to specify at least one inquiry to be transmitted to a third party.

In additional embodiments of this and related aspects, the user interface presents a template to guide the capture of further images, and the template may be derived from previously-captured images.

In additional embodiments of this and related aspects, the apparatus includes a processor configured to analyze a plurality of images and thereby derive information concerning a medical condition, which in certain embodiments may be a skin condition.

In another aspect, the present invention relates to a method for remote medical follow-up. According to this aspect and related aspects, the method includes the steps of prompting a first user on a predetermined schedule to capture an image of a physical expression of a medical condition, transmitting the captured images for subsequent viewing by at least one second user, and presenting the at least one second user with the captured images to permit the at least one second user to evaluate the medical condition. In certain embodiments, the medical condition is a skin condition. In certain embodiments, the predetermined schedule is a predetermined interval.

In additional embodiments of this and related aspects, the method includes the further steps of presenting the first user with at least one inquiry concerning a symptom of the medical condition, receiving a response to the at least one inquiry from the first user, and providing the response to the at least one second user.

In additional embodiments of this and related aspects, the captured images are presented to the at least one second user as a gallery or a time-lapse sequence. The method may further include the step of presenting the first user with a template of the physical expression to guide the first user in the capture of the image. In certain embodiments, the template is derived from previously-captured images. In additional embodiments, the template can be presented as a shadow overlay. In some embodiments, the method further includes prompting a first user to calibrate an image capture facility by capturing an image of a known object.

In another embodiment of this and related aspects, the method may include presenting the at least one second user with information computationally derived from the plurality of images to assist the at least one second user in the evaluation of the medical condition. In yet another embodiment, presenting the at least one second user with the captured images includes selecting at least one image from the captured images utilizing machine learning and presenting the at least one selected image to the at least one second user.

In another aspect, the present invention concerns an apparatus for remote medical follow-up. According to this aspect and related aspects, the apparatus includes an interface configured to receive communications from a first apparatus, the communications comprising at least one of personal information and a photo frequency, wherein the interface is further configured to transmit communications to the first apparatus, the communications comprising at least one of an identifier and an image, wherein the interface is further configured to receive communications from a second apparatus, the communications comprising at least one of the identifier, the image, and a response to an inquiry, and wherein the interface is further configured to transmit communications to a second apparatus, the communications comprising at least one of the photo frequency and the inquiry.

These and other features and advantages, which characterize the present non-limiting embodiments, will be apparent from a reading of the following detailed description and a review of the associated drawings. It is to be understood that both the foregoing general description and the following detailed description are explanatory only and are not restrictive of the non-limiting embodiments as claimed.

BRIEF DESCRIPTION OF DRAWINGS

Non-limiting and non-exhaustive embodiments are described with reference to the following Figures in which.

In the drawings, like reference characters generally refer to corresponding parts throughout the different views. The drawings are not necessarily to scale, emphasis instead being placed on the principles and concepts of operation.

DETAILED DESCRIPTION OF THE INVENTION

Various embodiments are described more fully below with reference to the accompanying drawings, which form a part hereof, and which show specific exemplary embodiments. However, embodiments may be implemented in many different forms and should not be construed as limited to the embodiments set forth herein; rather, these embodiments are provided so that this disclosure will be thorough and complete, and will fully convey the scope of the embodiments to those skilled in the art. Embodiments may be practiced as methods, systems or devices. Accordingly, embodiments may take the form of a hardware implementation, a software implementation or an implementation combining software and hardware aspects. The following detailed description is, therefore, not to be taken in a limiting sense.

Embodiments of the present invention facilitate follow-up medical treatment while alleviating the need for patient and physician to be co-located. In fact, embodiments of the present invention enable additional forms of follow-up that simply are not possible absent placing a patient in a monitored environment for around-the-clock supervision. For example, embodiments of the present invention permit a physician to effectively evaluate, e.g., the healing of surgical sites or other skin conditions for an outpatient on a predetermined schedule.

Utilizing sensing and imaging technologies, embodiments of the present invention permit an individual to capture images, video, audio, and other relevant information for transmission to a health care provider. The health care provider can evaluate the transmitted information in lieu of requiring the patient to be physically present. The health care provider can also easily share the transmitted information among, e.g., other physicians on the patient's care team or remotely located specialists as needed.

Communications between the physician and the patient are bidirectional, permitting the physician to solicit additional information from the patient to help with the diagnostic process. For example, the physician can provide the patient with a list of follow-up questions that the patient can answer.

Embodiments of the present invention include various security mechanisms including, but not limited to, authentication mechanisms and encryption to secure physician and patient data as is often required by local policy and law.

Figure 1:
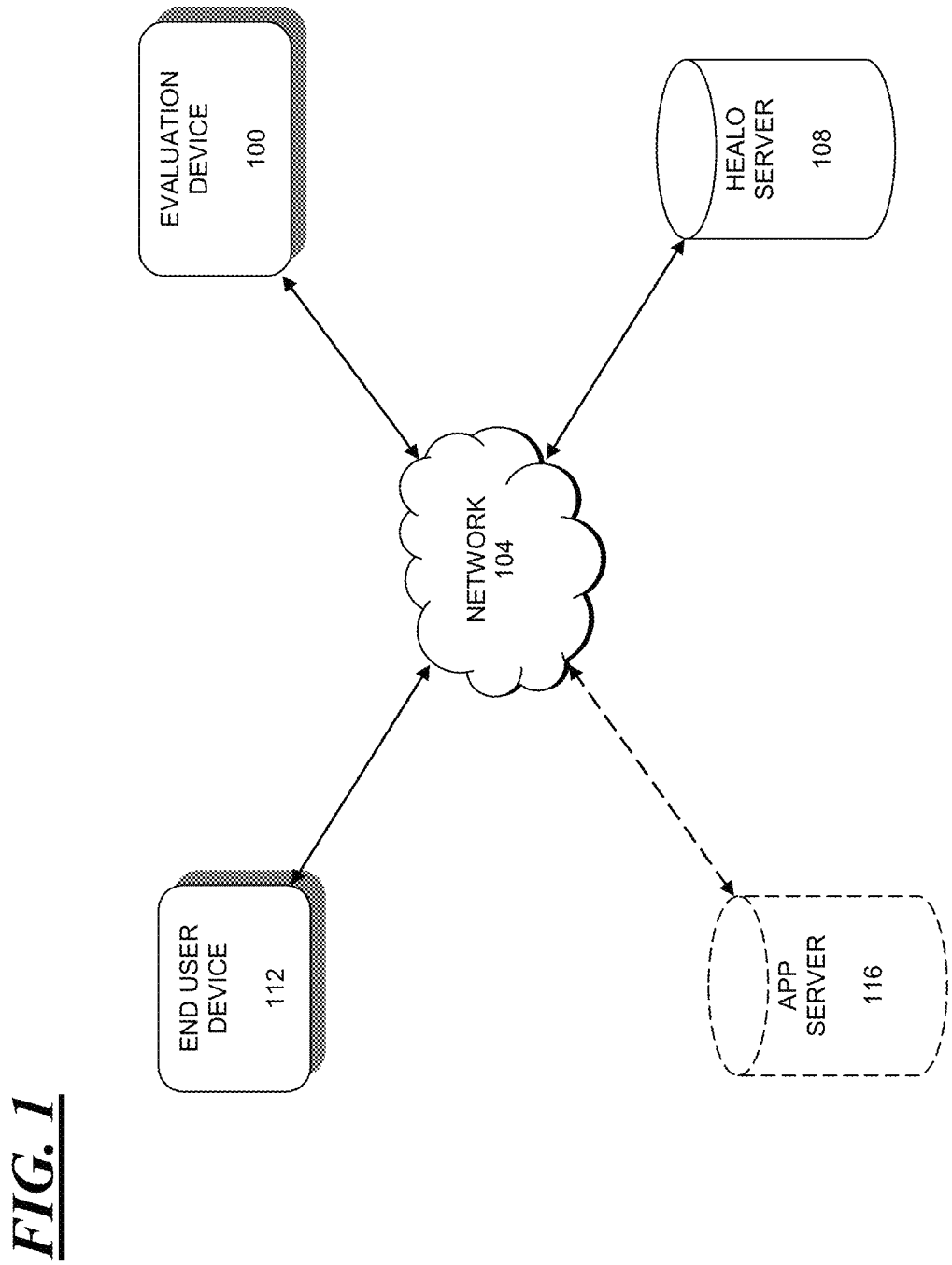
FIG. 1 is a block diagram illustrating one embodiment of a system in accord with the present invention.

FIG. 1 illustrates a typical embodiment of the invention. A healthcare provider such as a physician, nurse practitioner or trained specialist operates one or more evaluation devices 100 to interact with their patients and the apparatus that provides the functionality of the present invention. The evaluation device 100 typically takes the form of a computing device such as a desktop computer or a laptop computer, although any device with a suitable interface and network connectivity such as a smartphone or tablet can be used.

The evaluation device 100 is in contact with a network 104 such as the Internet or a wide-area network utilizing, e.g., a wired or wireless interface. The form of interface may vary depending on the particular nature of the evaluation device 100. Typical interfaces include gigabit Ethernet, Wi-Fi (802.11a/b/g/n), and 3G/4G wireless interfaces such as GSM/WCDMA/LTE that enable data transmissions between evaluation device 100 and other devices in communication with the network 104.

Like evaluation device 100, the HEALO server 108 is also in communication with the network 104. The name "HEALO server" is meant to identify the server by its role in various embodiments of the present invention. It is not intended to convey any particular limitation or restriction concerning the underlying technologies implementing the HEALO server 108. In particular, various implementations of the HEALO server 108 include physical server machines such as a locally-hosted server computer, a remotely-hosted blade server, locally or remotely hosted clusters of servers, a virtual machine hosted by an on-demand computing service such as ELASTIC COMPUTE CLOUD a.k.a. EC2 offered by AMAZON.COM, INC. of Seattle, Wash., etc.

The patient seeking medical care operates an end user device 112 in accord with the present invention. Like the evaluation device 100, the end user device 112 is typically some form of computing device such as a desktop computer, a laptop computer, a smartphone, or a tablet, although, as discussed in greater detail below, the end user device 112 should either include or be capable of being equipped with various sensing means to permit relevant measurements to be performed to permit the healthcare provider to diagnose the patient's condition. As discussed below, useful sensing means include cameras, such as visible light and infrared cameras, thermometers, etc.

Various embodiments of the invention may include additional computing resources to assist the operation of the evaluation device 100 and the end user device 112 in accord with the present invention. For example, some embodiments utilize an app server 116 to distribute software for installation on evaluation devices 100 and end user devices 112. The app server 116 may be operated by the provider of the HEALO server 108 or it may be offered by a third party. The app server 116 may be a commercial app service such as the GOOGLE PLAY STORE offered by GOOGLE, INC. of Mountain View, Calif., or the APP STORE offered by APPLE, INC. of Cupertino, Calif.

Figure 2:
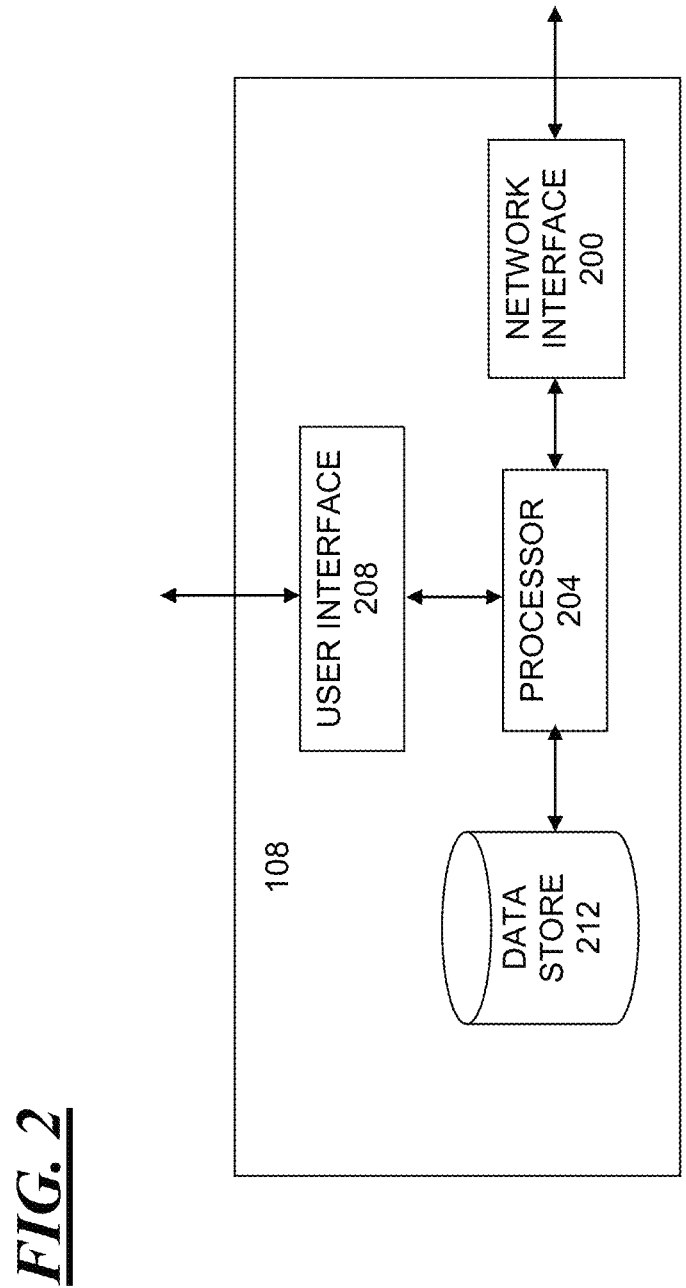
FIG. 2 depicts the HEALO server 108 of FIG. 1 in more detail.

FIG. 2 describes the HEALO server 108 in additional detail. As discussed above, the HEALO server 108 can take various forms, physical and virtual, but most implementations will share certain common functionalities. The network interface 200 allows the HEALO server 108 to receive communications from other devices and, in one embodiment, provides a bidirectional interface to the Internet. Suitable network interfaces 200 include gigabit Ethernet, Wi-Fi (802.11a/b/g/n), and 3G/4G wireless interfaces such as GSM/WCDMA/LTE that enable data transmissions between HEALO server 108 and other devices. A processor 204 generates communications for transmission through the interface 200 and processes communications received through the interface 200 that originate outside the HEALO server 108. A typical processor 204 is an x86, x86-64, or ARMv7 processor, and the like. The user interface 208 allows the HEALO server 108 to receive commands from and provide feedback to an operator. Exemplary user interfaces include graphical displays, physical keyboards, virtual keyboards, etc. The data store 212 provides both transient and persistent storage for data received via the interface 200, data processed by the processor 204, and data received or sent via the user interface 208.

The interface 200 of the HEALO server 108 is configured to handle communications among various evaluation devices 100 and end user devices 112. The HEALO server 108 receives communications from evaluation devices 100 such as communications including patient personal information and schedules for patient image capture. The HEALO server 108 in turn communicates with the evaluation devices 100, sending them such information as a unique identifier associated with a particular patient and one or more images provided by a patient. The HEALO server 108 receives communications from end user devices 112 including such information as an identifier associated with a particular patient, an image taken by a patient, and a response from the patient to a physician-provided inquiry. The HEALO server 108 in turn communicates with the end user devices 112, providing such information as physician-provided inquiries and schedules for image capture for the patient associated with a particular end user device 112.

Figure 3:
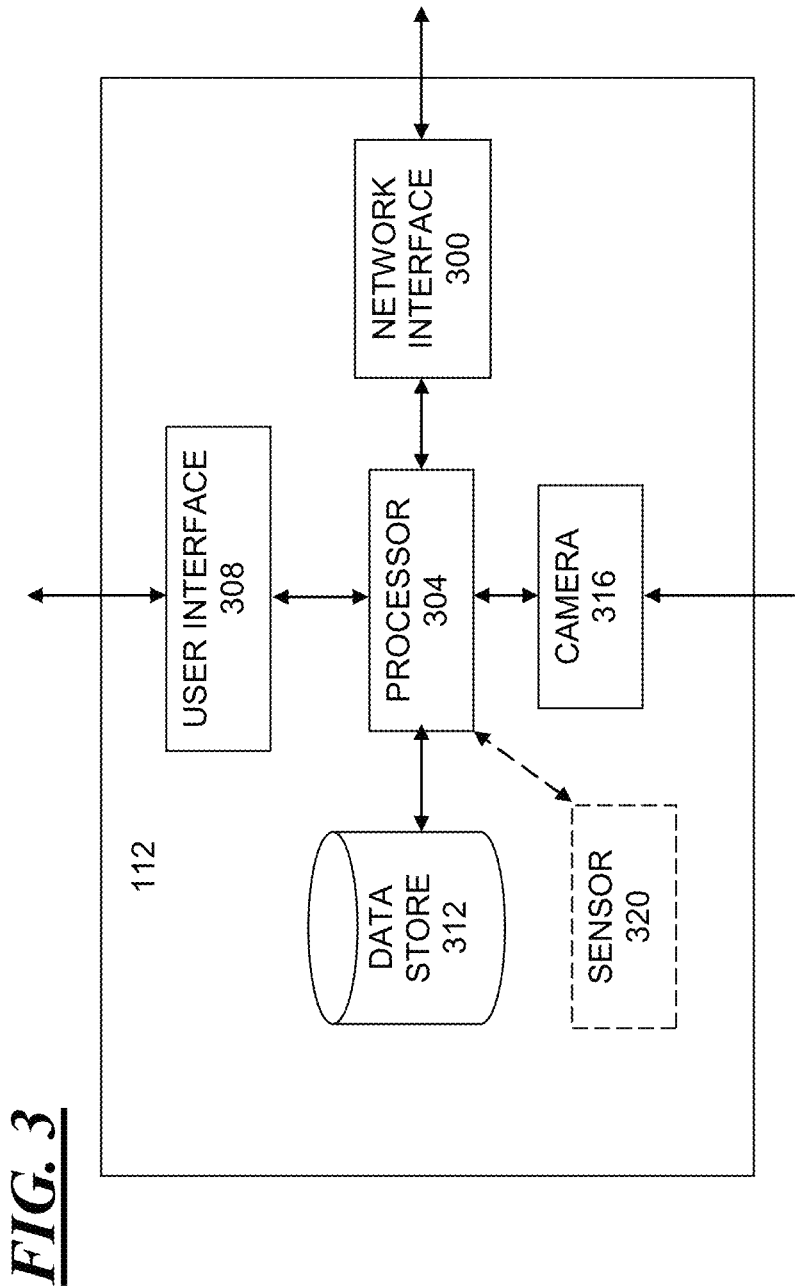
FIG. 3 presents the end user device 112 of FIG. 1 in more detail.

FIG. 3 describes the end user device 112 in additional detail. As discussed above, the end user device 112 and the HEALO server 108 are typically implemented using different technologies. For example, a HEALO server 108 may be an array of virtual machines operating on a commercial cloud computing service, while a typical end user device 112 may be an iPhone or other smartphone device. Despite the differences in implementing technologies, a typical end user device will possess or offer some of the same facilities present in the HEALO server 108.

For example, the network interface 300 allows the end user device 112 to receive communications from other devices and, in one embodiment, provides a bidirectional interface to the Internet. Suitable network interfaces 300 include gigabit Ethernet, Wi-Fi (802.11a/b/g/n), and 3G/4G wireless interfaces such as GSM/WCDMA/LTE that enable data transmissions between end user device 112 and other devices. A processor 304 generates communications for transmission through the interface 300 and processes communications received through the interface 300 that originate outside the end user device 112. A typical processor 304 is an x86, x86-64, or ARMv7 processor, and the like. The user interface 308 allows the end user device 112 to receive commands from and provide feedback to an operator. Exemplary user interfaces include graphical displays, physical keyboards, virtual keyboards, etc. The data store 312 provides both transient and persistent storage for data received via the interface 300, data processed by the processor 304, and data received or sent via the user interface 308.

The end user device 112 typically differs from the HEALO server 108 and the other computing facilities involved in the invention (e.g., app server 116) in that it includes at least a camera 316 and may include other pertinent sensing functionalities 320. The operator of the end user device 112 may operate the camera 316 using the user interface 308 to capture one or more images or video clips that may be, e.g., stored in the data store 312 or transmitted over the network 104 using the network interface 300. In particular, images and video captures by the camera 316 may be transmitted over the network 104 to HEALO server 108 for later review, as discussed in greater detail below. The additional sensing functionalities 320 will typically vary among end user devices 112, but may include such functionalities 320 as a thermometer, a galvanometer, a pH sensor, a glucometer, etc.

In certain embodiments, the end user device 112 may use the user interface 308 to prompt the patient to provide additional information to assist in the evaluation process. For example, the patient may be asked to respond to a multiple choice question or to an open-ended question. When the user interface 308 is, e.g., a touch-sensitive screen that can both present information to the patient and receive information from the patient using a virtual keyboard, the patient may respond to these further solicitations using the user interface 308. The end user device 112 may allow the patient to, in turn, provide questions for the healthcare professional to answer using, e.g., user interface 308 in a similar manner.

While many patients may be familiar with the operation of camera 316, there are certain steps that can be taken in connection with the capturing of the image to facilitate later review and diagnosis by the treating healthcare professional. For example, it helps to maintain the same orientation and distance from the same area of interest. The patient can be coached through these steps in several ways. First, the treating healthcare professional can personally instruct the patient and demonstrate the proper operation of the camera. Second, the software installed on the end user device 112 may itself instruct the patient and guide the patient through the image capture process. Third, the software installed on the end user device 112 may actively analyze the orientation of the camera 316 while the patient is operating the device 112 and provide the patient with feedback when the camera 316 is properly oriented. Fourth, the software installed on the end user device 112 may analyze previously-captured images and use the captured images to generate guide marks or a silhouette that may be displayed as an overlay to the camera frame; the patient can change the orientation of the camera 316 to align the scene for imaging with the silhouette.

While end user device 112 may include camera functionality, it is known that such functionality may not be the equivalent of a dedicated camera device. For example, the end user device 112 may rely on an digital zoom feature in lieu of a physical optical zoom device and it may suffer from a slow "shutter speed" if, e.g., the end user 112 has a low-end processor. In particular, if the camera functionality of the end user device 112 has slow or poor focusing then, in accord with the present invention, the end user device 112 may prompt the patient to take a picture of a known object (e.g., a quarter, a colored sticker) to permit the software executing on the end user device 112 to correct for the hardware deficiencies of the camera 316 on the end user device 312.

Embodiments of the present invention may also embed information in captured images (e.g., focal length, other EXIF data, or both) that may be used to normalize images in a post-processing stage or to guide the capture of further images. For example, a focal length parameter embedded in a first image may be used to prevent a patient from capturing an image that does not have substantially the same focal length. Developing a plurality of images having the same field of view (e.g., due to the use of shadow overlays for guidance) and similar focal lengths would permit the comparison of the sizes of various features of interest appearing in the images, such as the length of a wound and whether the wound is growing or shrinking in size.

With sufficient embedded information, e.g., focal length, light level, etc., the patient could be actively guided through the image capture process with feedback such as "move closer" or "find better lighting." The processor 304 on the end user device 112 may be configured to actively analyze the input from the camera sensor as the patient follows this feedback and to automatically capture the image when the current image values match up with the desired template, focal length, light level, etc. This functionality could lead to patients capturing images of features and conditions that they cannot directly observe, such as a suture region on their back.

Figure 4:
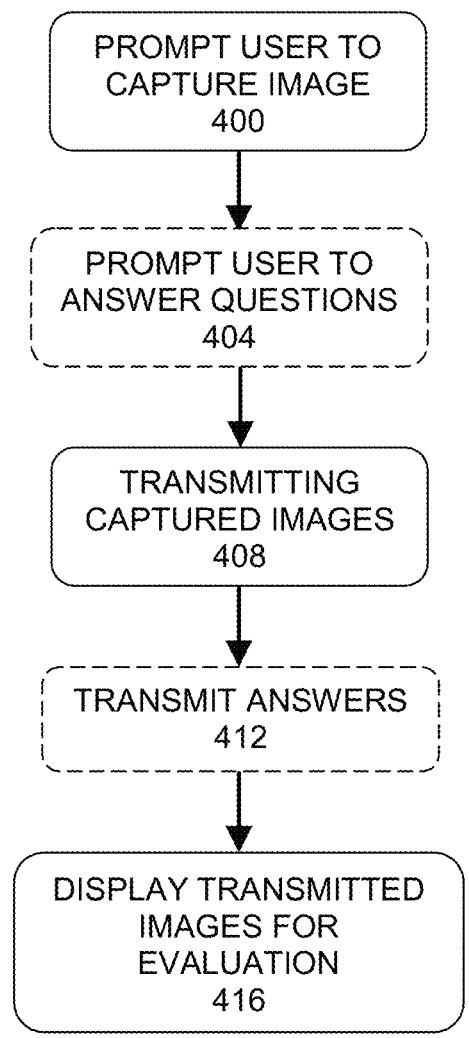
FIG. 4 presents one embodiment of a method for medical follow-up in accord with the present invention.

FIG. 4 presents an embodiment of a method for medical follow-up in accord with the present invention. A user is prompted to capture an image of a physical expression of a medical condition (Step 400). The prompting may occur pursuant to a predetermined schedule, such as once a day, once every three days, once a week, etc. The duration of the schedule may also be specified, such as, e.g., once a week for five weeks. The image may be a still image or, in other embodiments, a video clip.

As discussed above, the user may be guided in the image capture process through human instruction, automated instruction, automated feedback, guide marks, or a template derived from previously-captured images and presented as a shadow overlay to the current camera view.

In certain embodiments the user may be prompted to provide additional information, such as information concerning a symptom of the medical condition. This may involve, for example, responding to multiple choice questions or questions that require short typed or spoken answers (Step 404).

Once captured, those images are transmitted for later study and review (Step 408). In those embodiments where the user provides additional information, that information is also transmitted for later review (Step 412).

At some point, the healthcare professional may want to review the transmitted images to evaluate the patient's progress. The previously-transmitted images may be displayed to the healthcare professional (Step 416) in the form of a gallery, i.e., where all of the images are presented juxtaposed in a grid format, in a timeline, or in some form of time-lapse sequence.

In some embodiments, the images may be processed prior to transmission or after transmission to derive information to assist in evaluation of the medical condition. Post-processing may identify images where certain absolute criteria are met, such as a certain number of pixels having a certain hue, etc. Post-processing may also identify images where certain relative criteria are met, such as a certain number of pixels that differ between images, or changes that emerge in subsequent images that are not present in earlier images, etc. One particular image may be identified and presented to the healthcare professional or other feedback may be provided.

Figure 5A:
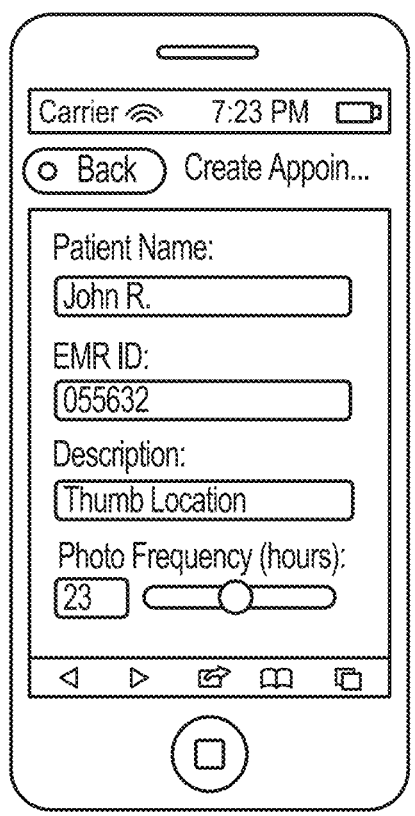
FIGS. 5A, 5B, and 5C illustrate how another embodiment of a system in accord with the present invention can be utilized to perform medical follow-up.
Figure 5A:
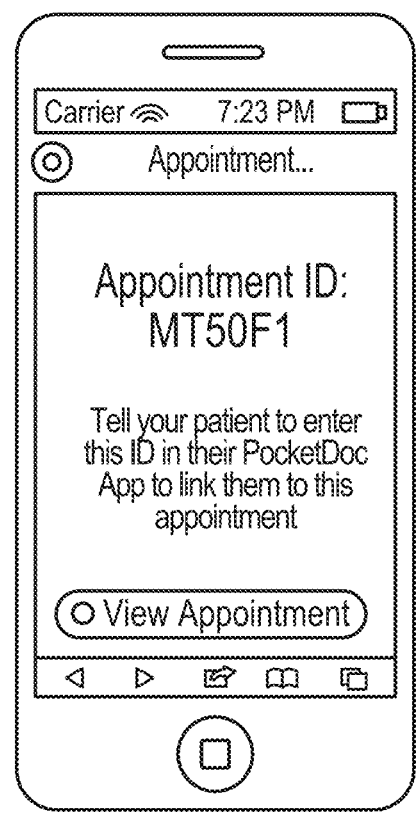
Figure 5B:
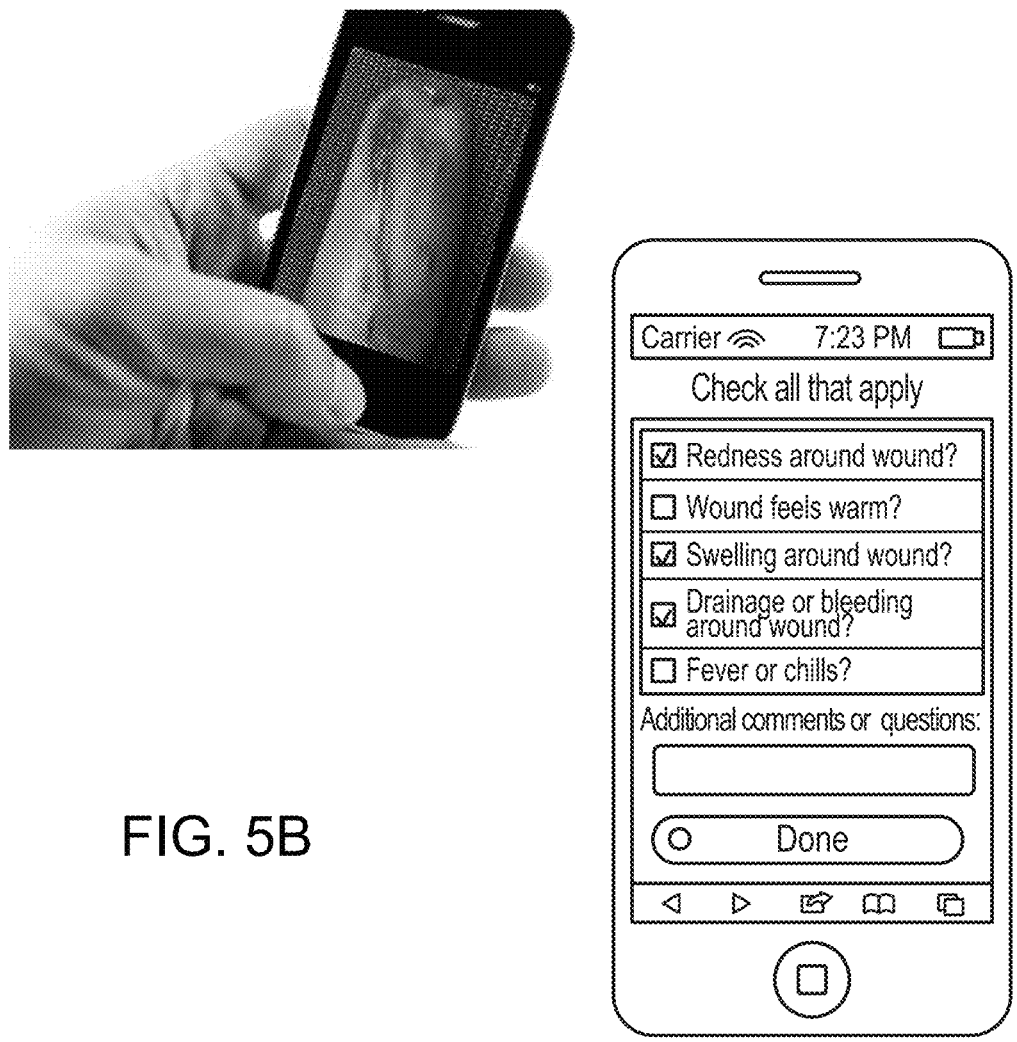
Figure 5C:
Figure 5C:
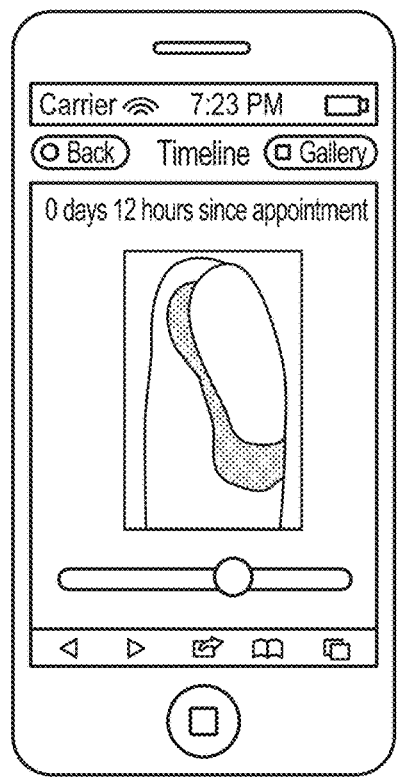
Figure 5C:
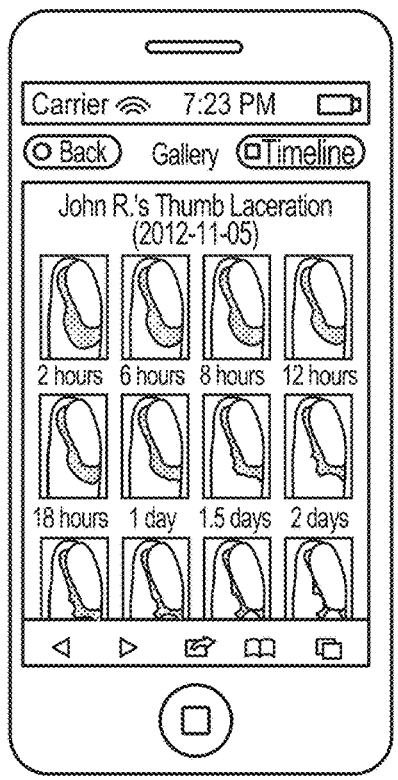
Figure 5C:
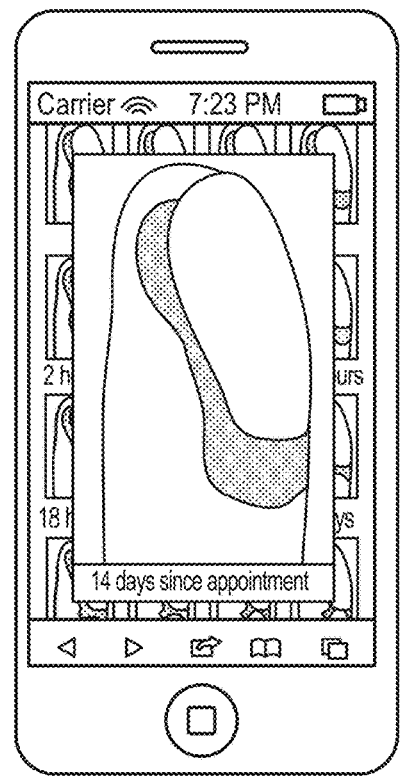

FIGS. 5A, 5B, and 5C depict one example of a use case involving an embodiment of the present invention. In this example, a physician treats a patient for a thumb laceration and desires to monitor the healing of the stitched wound. This would normally require at least one follow-up visit by the patient to the physician's office.

With reference to FIG. 5A, the physician begins the process by operating his evaluation device, in this case, a mobile phone, to activate a HEALO app installed on the device. The physician enters some basic information concerning the patient and the desired frequency for the patient to take photos. The HEALO app on the evaluation device communicates the information to software installed on the HEALO server and receives an appointment ID for the patient.

The physician gives the appointment ID to the patient and asks the patient to install the HEALO app on their end user device. The patient installs the HEALO app and enters the appointment ID, at which point the HEALO app prompts the patient to capture images on the specified schedule. As depicted in FIG. 5B, the HEALO app can guide the patient through the image capture process using various mechanisms, such as a shadow overlay.

With continued reference to FIG. 5B, in certain embodiments the physician may specify additional questions for the patient to answer and, in turn, the patient may provide feedback and questions for the physician to answer.

With reference to FIG. 5C, after the images are captured they are transmitted for later review by the physician. The physician can review each image individually, zooming in as desired to examine particular regions of the photograph. The images can be reviewed collectively as a scrollable timeline or a gallery.

Embodiments of the present disclosure, for example, are described above with reference to block diagrams and/or operational illustrations of methods, systems, and computer program products according to embodiments of the present disclosure. The functions/acts noted in the blocks may occur out of the order as shown in any flowchart. For example, two blocks shown in succession may in fact be executed substantially concurrent or the blocks may sometimes be executed in the reverse order, depending upon the functionality/acts involved. Additionally, not all of the blocks shown in any flowchart need to be performed and/or executed. For example, if a given flowchart has five blocks containing functions/acts, it may be the case that only three of the five blocks are performed and/or executed. In this example, any of the three of the five blocks may be performed and/or executed.

The description and illustration of one or more embodiments provided in this application are not intended to limit or restrict the scope of the present disclosure as claimed in any way. The embodiments, examples, and details provided in this application are considered sufficient to convey possession and enable others to make and use the best mode of the claimed embodiments. The claimed embodiments should not be construed as being limited to any embodiment, example, or detail provided in this application. Regardless of whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the general inventive concept embodied in this application that do not depart from the broader scope of the claimed embodiments.

What is claimed is:

1. A method for remote medical follow-up, the method comprising:
    prompting a first user on a predetermined schedule to capture at least one image of a physical expression of a medical condition;
    presenting the first user with a template in the form of a shadow overlay based on at least one previously captured image of a previous physical expression of the first user's medical condition to guide the first user in the capture of the at least one image;
    transmitting the at least one captured image for subsequent viewing by at least one second user; and
    presenting the at least one captured image to the at least one second user to permit the at least one second user to evaluate the medical condition.

2. The method of claim 1 further comprising:
    presenting the first user with at least one inquiry concerning a symptom of the medical condition;
    receiving a response to the at least one inquiry from the first user; and
    providing the response to the at least one second user.

3. The method of claim 1 wherein the at least one captured image is presented to the at least one second user as a gallery or a time-lapse sequence.

4. The method of claim 1 further comprising presenting the at least one second user with information computationally derived from a plurality of images to assist the at least one second user in the evaluation of the medical condition.

5. The method of claim 1 wherein the medical condition is a skin condition.

6. The method of claim 1 wherein the predetermined schedule is a predetermined interval.

7. The method of claim 1 wherein presenting the at least one second user with the at least one captured image to permit the at least one second user to evaluate the medical condition comprises selecting at least one image from the captured images utilizing machine learning and presenting said at least one selected image to the at least one second user.

8. The method of claim 1 further comprising prompting the first user to calibrate an image capture facility by capturing an image of a known object.

* * * * *